United States Patent
Smith

(10) Patent No.: US 7,642,372 B2
(45) Date of Patent: Jan. 5, 2010

(54) PROCESS FOR PREPARING CARBOXYLIC ACIDS AND DERIVATIVES THEREOF

(75) Inventor: Warren John Smith, East Riding (GB)

(73) Assignee: BP Chemicals Limited, Middlesex (GB)

( * ) Notice: Subject to any disclaimer, the term of this patent is extended or adjusted under 35 U.S.C. 154(b) by 147 days.

(21) Appl. No.: 11/578,718

(22) PCT Filed: Mar. 24, 2005

(86) PCT No.: PCT/GB2005/001202

§ 371 (c)(1),
(2), (4) Date: Sep. 13, 2007

(87) PCT Pub. No.: WO2005/105720

PCT Pub. Date: Nov. 10, 2005

(65) Prior Publication Data

US 2008/0091046 A1  Apr. 17, 2008

(30) Foreign Application Priority Data

Apr. 28, 2004 (GB) ................................. 0409490.0

(51) Int. Cl.
*C07C 67/36* (2006.01)
*C07C 51/12* (2006.01)
*B01J 29/04* (2006.01)
*B01J 29/18* (2006.01)

(52) U.S. Cl. .................. 560/232; 562/519; 502/61; 502/78

(58) Field of Classification Search ................ None
See application file for complete search history.

(56) References Cited

U.S. PATENT DOCUMENTS

| 4,612,387 | A | | 9/1986 | Feitler |
| 5,420,345 | A | * | 5/1995 | Smith ................. 562/519 |
| 7,309,798 | B2 | * | 12/2007 | Cheung et al. ......... 560/232 |
| 7,465,822 | B2 | * | 12/2008 | Cheung et al. ......... 560/232 |

FOREIGN PATENT DOCUMENTS

| EP | 0 030 110 A1 | 6/1981 |
| EP | 0 453 148 A1 | 10/1991 |
| EP | 0 596 632 A1 | 5/1994 |

OTHER PUBLICATIONS

Patent Abstracts of Japan, vol. 2002, No. 10; Oct. 10, 2002 & JP 2002 160916 A (Tosho Corp.) Jun. 4, 2002 (Abstract).
Fricke, Rolf, et al; "Incorporation of Gallium into Zoelites: Synthesis, Properties and Catalytic Application"; *Chem. Rev.*, 2000; vol. 100, pp. 2303-2405; XP-002336180.

* cited by examiner

*Primary Examiner*—Paul A Zucker
(74) *Attorney, Agent, or Firm*—Nixon & Vanderhye

(57) ABSTRACT

Preparation of an aliphatic carboxylic acid having (n+1) carbon atoms, where n is an integer up to 6, and/or an ester or anhydride thereof may be achieved by contacting an aliphatic alcohol having n carbon atoms and/or a reactive derivative thereof with carbon monoxide substantially in the absence of the halogens or derivatives thereof at a temperature in the range 250-600° C. and at a pressure in the range 10 to 200 bars, in the presence of a catalyst consisting essentially of a mordenite which has, as framework elements, silicon, aluminum and one or more of gallium, boron and iron, and which has been ion-exchanged or otherwise loaded with copper, nickel, iridium, rhodium or cobalt.

25 Claims, No Drawings

PROCESS FOR PREPARING CARBOXYLIC ACIDS AND DERIVATIVES THEREOF

This application is the U.S. National Phase of International Application PCT/GB2005/001202, filed 24 Mar. 2005, which designated the U.S. PCT/GB2005/001202 claims priority to British Application No. 0409490.0 filed 28 Apr. 2004. The entire content of these applications are incorporated herein by reference.

The present invention relates to a process for preparing an aliphatic carboxylic acid and/or derivatives thereof by reacting the corresponding alcohol or a reactive derivative thereof with carbon monoxide in the presence of a metal loaded mordenite catalyst.

The preparation of acetic acid from methanol and carbon monoxide is a well known carbonylation process and is one which is carried out commercially. On a commercial scale the manufacture of acetic acid may be operated as a homogeneous liquid-phase process in which the carbonylation reaction is catalysed by a soluble rhodium/iodide complex and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

GB 1185453 discloses certain multiphase catalysts comprising a catalytically active metal including inter alia copper, rhodium and iridium supported on a wide range of carrier materials including silicas, aluminas, carbons, zeolites, clays and polymers. These multiphase catalysts are taught as being useful in the heterogeneous gas phase carbonylation of methanol to acetic acid in the presence of a halide promoter. A similar process is disclosed GB 1277242, although neither patent exemplifies the use of zeolites in such a process.

U.S. Pat. No. 4,612,387 discloses a process for making monocarboxylic acids and esters comprising contacting carbon monoxide with a monohydric alcohol having from 1 to 4 carbon atoms in the presence of a crystalline aluminosilicate zeolite having a silica to alumina ratio of at least about 6 and a constraint index within the range of 1 to 12 under a pressure of at least 1 atmosphere. The most preferred zeolites according to this definition are ZSM-5, ZSM-11, ZSM-12, ZSM-38 and ZSM-35 with ZSM-5 being particularly preferred. Mordenite type zeolites, which have a constraint index of 0.4, are referred to in Example VI run 30 where the hydrogen form was shown not to be catalytically effective. The preferred zeolites are preferably modified to incorporate a Group IB, IIB, IVB or VIII metal, of which the most preferred is copper.

J Catalysis, 71, 233-43 (1981) discloses the use of photoelectron spectroscopy (ESCA) to determine the activity of a rhodium mordenite catalyst and other supported rhodium catalysts towards carbonylation of methanol to acetic acid.

DE 3606169 discloses a process for the preparation of acetic acid, methyl acetate and/or dimethyl ether by carbonylation of anhydrous methanol, methyl acetate and/or dimethyl ether in the presence of cobalt containing zeolites or zeolites mixed with cobalt salts. The carbonylation is optionally carried out in the presence of a halide. The preferred zeolites are disclosed as being of the pentasil type whose pore sizes are intermediate between that of zeolite A on the one hand and zeolites X and Y on the other.

Chemistry Letters pp 2047-2050 (1984) is concerned with the vapour phase carbonylation of methanol in the absence of a halogen promoter. Table 1 of this paper refers to three examples carried out at 200° C. and 10 bar pressure in which hydrogen mordenite and copper mordenite are used as catalysts. In all three cases yields were low relative to similar experiments employing a ZSM-5 based catalyst.

EP 0596632 A1 discloses a process for the preparation of an aliphatic carboxylic acid by contacting an alcohol or a reactive derivative thereof with carbon monoxide, substantially in the absence of halogens or derivative thereof, in the presence of a catalyst consisting essentially of a mordenite zeolite which has been ion-exchanged or loaded with copper, nickel, iridium, rhodium or cobalt, characterised in that the process is carried out at a temperature in the range 300° to 600° C. and at a pressure in the range 15 to 200 bars.

Thus there remains a need for an improved heterogeneous gas phase process for preparing carboxylic acids and/or derivatives thereof from alcohols and/or reactive derivatives thereof and carbon monoxide using a metal loaded zeolite catalyst and which is carried out in the substantial absence of halogens or derivatives thereof.

It has now been found that a mordenite zeolite (hereinafter referred to as mordenite) which has been modified to include metals in addition to silicon and aluminium in the framework provides enhanced product selectivity (to acetic acid or derivatives thereof) and/or enhanced catalyst stability.

Accordingly, the present invention provides a process for preparing an aliphatic carboxylic acid having (n+1) carbon atoms, where n is an integer up to 6, and/or an ester or anhydride thereof which comprises contacting an aliphatic alcohol having n carbon atoms or a reactive derivative thereof with carbon monoxide substantially in the absence of the halogens or derivatives thereof and in the presence of a catalyst at a temperature in the range 250-600° C. and at a pressure in the range 10 to 200 bars, characterised in that the catalyst consists essentially of mordenite which has, as framework elements, silicon, aluminium and one or more of gallium, boron and iron, and which has been ion-exchanged or otherwise loaded with copper, nickel, iridium, rhodium or cobalt.

The process of the present invention utilises a modified mordenite catalyst at high temperatures and pressures to produce good yields of carboxylic acids and derivatives thereof. It has been surprisingly found that improved product selectivity and enhanced catalyst stability can be achieved by utilising a mordenite which has been modified by the addition of one or more of gallium, boron and iron (framework modifier elements) as a framework element, compared to a mordenite having silicon and aluminium as the only framework elements.

In the process of the present invention an aliphatic alcohol or a reactive derivative thereof is carbonylated with carbon monoxide. The process is particularly applicable to aliphatic alcohols having up to 6, such as up to 3, carbon atoms. A preferred alcohol is methanol.

Reactive derivatives of the alcohol which may be used as an alternative to, or in addition to the alcohol, include dialkyl ethers, esters of the alcohol and alkyl halides. Suitable reactive derivatives of methanol, for example, include methyl acetate, dimethyl ether and methyl iodide. A mixture of an alcohol and the reactive derivative thereof, for example a mixture of methanol and methyl acetate, may also be employed.

In one embodiment, where methanol is to be employed as the alcohol, the methanol may be used as such or it may be generated from a source of carbon monoxide and hydrogen, such as the commercially available synthesis gas, in the presence of a suitable alcohol synthesis catalyst. Suitable methanol synthesis catalysts are described, for example, in WO 99/38836 and WO 01/07393. A specific example of a suitable methanol synthesis catalyst is a copper/zinc oxide catalyst with or without an aluminium promoter. The methanol synthesis may be carried out in situ or in a separate reactor from the carbonylation process of the present invention.

The product of the carbonylation process may be an aliphatic carboxylic acid and may also comprise the ester of the aliphatic carboxylic acid. For example, where the alcohol is methanol the product comprises acetic acid and may also comprise methyl acetate. The ester may be converted to the aliphatic carboxylic acid by known methods. The process of the present invention may also be applied to the synthesis of propionic acid from ethanol and also butanoic acid from n-propanol.

The process may be carried out in the presence or substantial absence of water. Where a reactive derivative such as an ester or an ether, is used as the feed, water is preferably also fed to the reaction. For example, where dimethyl ether is used as the feed, water is also fed to the reaction, such as in a water:dimethyl ether mole ratio of greater than 0 to less than or equal to 1.

The purity of the carbon monoxide used is not deemed to be especially critical although it is desirable to use gas mixtures in which carbon monoxide is the main component. The presence of small amounts of impurities such as nitrogen and the noble gases can be tolerated. In addition, mixtures of carbon monoxide and hydrogen as produced by the reforming or partial oxidation of hydrocarbons (synthesis gas) may also be used in the process of the present invention.

The catalyst used in the process of the present invention is a modified mordenite zeolite which has been ion-exchanged, or otherwise loaded with copper, nickel, iridium, rhodium or cobalt. The structure of mordenite is well known and defined for example in 'Atlas of Zeolite Structure Types' by W M Meier and D H Olson published by the Structure Commission of the International Zeolite Association in 1978. It is further characterised by having a constraint index of 0.4 and a silica to alumina ratio in the range 8:1 to 20:1. It is well known to those skilled in the art that the silica to alumina ratio may be increased by using de-alumination techniques, for example, by hydro-thermal treatment or acid leaching of the mordenite. Mordenite also possesses a characteristic X-ray powder diffraction pattern which will be well known to those skilled in the art. For the process of the present invention it is preferred that the mordenite has a silica to alumina ratio in the range 8:1 to 50:1, preferably in the range 10:1 to 30:1 and most preferably in the range 15:1 to 25:1.

The framework modifier elements (gallium, boron and/or iron) may be introduced to the framework by any conventional means. For example, the mordenite may be synthesised using suitable precursors for the silicon, aluminium and gallium, iron and/or boron components of the framework, such as, for a gallium modified mordenite, by reacting together a mixture comprising fumed silica, gallium nitrate and sodium aluminate.

For the process of the present invention it is preferred that the mordenite has a ratio of silica to the oxides of the framework modifier elements (i.e. total of gallium oxide, boron oxide and iron oxide) in the range 10:1 to 50:1, preferably in the range 20:1 to 50:1, and more preferably in the range 30:1 to 40:1.

The framework modifier element is preferably gallium. Thus, it is preferred that the mordenite has a silica to gallium oxide ratio in the range 10:1 to 50:1, preferably in the range 20:1 to 50:1, and more preferably in the range 30:1 to 40:1.

Before use as a catalyst, the mordenite is ion-exchanged or otherwise loaded with copper, nickel, rhodium, iridium or cobalt. If the mordenite is to be ion-exchanged up to 80% of the cation-exchangable sites on the zeolite may be exchanged with e.g. $Cu^{2+}$, $Ir^{3+}$ or $Rh^{3+}$ ions using well known techniques. It is preferred that the remaining cations in the exchanged mordenite are protons hence it is convenient to start the exchange process from the ammonium or hydrogen form.

As an alternative to ion-exchange, the ammonium or hydrogen form of the mordenite can be impregnated with a solution of the salt of the metal and subsequently dried. If the ammonium form is used, it is preferred to calcine the mordenite after loading or exchange. The amounts used are preferably such as to produce a catalyst having a metal content of 0.5 to 10% by weight based on the total catalyst.

Preferably, the mordenite catalyst is activated prior to use by, for example, subjecting the mordenite catalyst for at least one hour at elevated temperature under flowing nitrogen, carbon monoxide or hydrogen.

The process of the present invention is preferably carried out by passing methanol vapour and carbon monoxide gas through a fixed or fluidised bed of the catalyst maintained at the required temperature and pressure. Such a process is carried out substantially in the absence of iodide. By substantially is meant that the iodide content of the feed gases and catalyst are less than 500 ppm and preferably less than 100 ppm.

The process is carried out at a temperature in the range 250 to 600° C., preferably 250 to 400° C., and at a pressure in the range 10 to 200 bars, preferably 10 to 150 bars, such as 25 to 100 bars.

The molar ratio of carbon monoxide to methanol is suitably in the range 1:1 to 60:1, preferably 1:1 to 30:1, most preferably 2:1 to 10:1. If fed to the catalyst bed in liquid form, the Liquid Hourly Space Velocity (LHSV) of the methanol feed should preferably be in the range 0.5 to 2.

The carboxylic acid produced by the process of the present invention can be removed in the form of a vapour and thereafter condensed to a liquid. The carboxylic acid can be subsequently purified using conventional techniques, such as distillation.

The invention will now be illustrated with reference to the following Examples.

EXAMPLES

Mordenite Synthesis

Comparative Example A

Ga Mordenite Synthesis

Tetraethyl ammonium bromide (TEA) (9.47 g) was dissolved in 30 g of distilled water and then added to a slurry of 22.26 g of fumed silica (Cab-O-Sil) in 150 g of distilled water. The resultant mixture was thoroughly agitated. A solution of sodium hydroxide (6.75 g) in 30 g of distilled water was added to the slurry and the mixture was then stirred for one hour. After this period a solution of gallium nitrate was prepared by dissolving 7.53 g of gallium nitrate in 70 g of distilled water. The gallium nitrate solution was then added to the silica slurry and the resultant gel stirred for a further 1 hour. The gel stoichiometry was calculated to be:

$$25.2SiO_2 \cdot 1.0Ga_2O_3 \cdot 5.7\ Na_2O \cdot 3.0TEABr \cdot 1054H_2O$$

The gel was then transferred into a stainless steel autoclave and heated at 150° C. for 16 days. After this period the autoclave was cooled and the contents filtered and washed with copious amounts of distilled water. The white solid was then dried at 120° C. overnight.

X-ray diffraction analysis showed the material to be highly crystalline and have a mordenite structure. Chemical analysis revealed the material to have a framework composition of $SiO_2/Ga_2O_3=31.1$.

Example 1

"Low Al" Ga/Al Mordenite Synthesis

A mordenite synthesis gel was prepared according to the method of Comparative Example A except that a mixture of gallium nitrate and sodium aluminate was added to the reaction mixture. This was achieved by adding a gallium nitrate solution (6.02 g dissolved in 35 g distilled water) and a sodium aluminate solution (0.50 g dissolved in 35 g distilled water) to the silica gel with vigorous stirring. After stirring for one hour the resultant gel was transferred to a stainless steel autoclave and heated at 150° C. for 11 days. The gel stoichiometry was calculated to be:

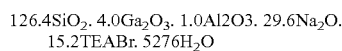
$126.4 SiO_2 . 4.0 Ga_2O_3 . 1.0 Al_2O_3 . 29.6 Na_2O . 15.2 TEABr . 5276 H_2O$ After this period the autoclave was cooled and the contents filtered and washed with copious amounts of distilled water. The white solid was then dried at 120° C. overnight.

X-ray diffraction analysis showed the material to be highly crystalline and have a mordenite structure. Chemical analysis revealed the mordenite zeolite to contain both framework gallium and aluminium and have the framework composition of $SiO_2/Ga_2O_3=32.6$ and a $SiO_2/Al_2O_3=102.4$.

Example 2

"High Al" Ga/Al Mordenite Synthesis

In this Example Ga/Al mordenite zeolite was synthesised with an increased amount of framework aluminium. The procedure of Example 1 was repeated except that the amount of sodium aluminate added was increased from 0.50 g to 2.88 g. The gel stoichiometry was calculated to be:

$48.5 SiO_2 . 1.5 Ga_2O_3 . 1.0 Al_2O_3 . 29.6 Na_2O . 15.2 TEABr . 5276 H_2O$

The resultant gel was heated at 150° C. for 14 days. The resultant crystalline solid was filtered, washed with copious amounts of water and dried at 120° C. overnight. X-ray diffraction analysis showed the material to be highly crystalline and have a mordenite structure. Chemical analysis revealed the mordenite zeolite to contain both framework gallium and aluminium and have the framework composition of $SiO_2/Ga_2O_3=39.2$ and a $SiO_2/Al_2O_3=19.4$.

Comparative Example B

"Low Al" Mordenite Synthesis

A "low Al" mordenite was prepared by acid leaching. 30 g of a commercially available mordenite zeolite (ex. PQ, CBV20A, $SiO_2/Al_2O_3=19.4$.) was refluxed for 2 hours in a hydrochloric acid solution prepared by diluting 24 ml of concentrated hydrochloric acid with 76 ml of distilled water. After this period the solid was filtered and washed with copious amounts of distilled water.

X-ray diffraction analysis showed that the material was still highly crystalline and had the mordenite structure. Chemical analysis revealed the material to have a framework composition of $SiO_2/Al_2O_3=36.0$.

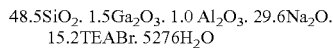

Comparative Example C

Al Mordenite

The commercially available mordenite zeolite (ex. PQ, CBV20A, $SiO_2/Al_2O_3=19.4$) was used as a further Comparative Example.

Catalyst Preparation

The synthesised mordenites of Comparative Example A and Examples 1 and 2 were calcined by heating the solids at 550° C. for 6 hrs to remove the organic template. The mordenites of Comparative Examples A to C and Examples 1 and 2 were converted into the ammonium form by contacting the solids with a 1.5M solution of ammonium nitrate solution at 80° C. for 3 hours before filtering and drying. The weight ratio of the 1.5M ammonium nitrate solution to mordenite used for the exchanges was 25:1. The exchange procedure was repeated three times for each mordenite.

The ammonium-form mordenites were converted into the copper loaded acid-forms by impregnating the mordenites with a copper solution followed by calcination. All the mordenites prepared had a nominal copper loading of approx. 7 wt/wt %.

The following procedure with reference to Comparative Example B is illustrative of the copper loading procedure. 23.04 g of the ammonium-form of the "low Al" mordenite prepared in Comparative Example B was added to a solution of copper nitrate trihydrate (6.33 g) in 140 g distilled water and stirred vigorously. The solution was evaporated to dryness by heating at 80° C. The blue solid was the calcined at 500° C. for 2 hours. Chemical analysis revealed the material to contain 6.6 wt/wt % Cu. The catalysts were then pelleted by crushing the copper loaded zeolites at 10 tonne in an infrared press and the resultant tablet broken and the material sieved to a size range of 250-850 microns.

Methanol Carbonylation

Each of the catalysts of Comparative Examples A to C and Examples 1 and 2 was used to catalyse the reaction of methanol and carbon monoxide in a single pass high-pressure microreactor. The catalyst volume used was typically 10 ml. A pre-bed of carborundum granules was used to provide efficient preheating of the reactants prior to contact with the catalyst. The catalysts were activated under flowing nitrogen (100 ml/min) at 350° C. for 16 hours and then reduced under carbon monoxide (200 ml/min) at 350° C. for 2 hours. The system was then pressurised up to 25 atm using a back-pressure regulator. The flow rate of the carbon monoxide was adjusted to 800 ml/min and methanol was fed to the reactor via a pump (rate=0.15 ml/min). The liquid and solid products were collected in a cooled trap, whilst gaseous products and reactants were sampled downstream of the back-pressure regulator.

The reaction was sampled every three hours. All of the samples were analysed by off-line gas chromatography. The level of carbon dioxide formed as a by-product from the competing water gas shift reaction was relatively low in all cases being in the range of 1 to 10 mol % of the total moles of product formed.

The results of the carbonylation experiments are given in Tables 1 to 3.

TABLE 1

Catalytic Performance of Cu/H—(Ga)Mordenite and Cu/H—(Ga, Al)Mordenites for methanol carbonylation

| Catalyst | Catalyst SiO$_2$/Ga$_2$O$_3$ | Catalyst SiO$_2$/Al$_2$O$_3$ | Reaction Time (hrs) | MeOH Conversion (%) | Product Selectivity (C-mol %) | | | |
|---|---|---|---|---|---|---|---|---|
| | | | | | DME | HC[i] | MeOAc | AcOH |
| Comparative Example A | 30.6 | — | 3 | 92.5 | 48.5 | 4.8 | 31.6 | 15.1 |
| | | | 7 | 88.7 | 82.7 | 1.1 | 13.5 | 5.4 |
| Example 1 | 32.6 | 102.4 | 3 | 99.5 | 0.0 | 22.8 | 6.9 | 68.2 |
| | | | 6 | 98.2 | 1.2 | 7.5 | 34.8 | 52.6 |
| Example 2 | 39.2 | 19.4 | 3 | 96.8 | 2.0 | 44.8 | 23.4 | 29.8 |
| | | | 6 | 97.0 | 4.2 | 3.1 | 49.2 | 42.9 |

Reaction Temperature = 350° C., Pressure = 25 barg, GHSV = 4400, CO/MeOH = 9, LHSV = 0.9
[i]HC = hydrocarbons The results in Table 1 demonstrate that the catalyst having a mordenite structure containing gallium (Comparative Example A) is capable of catalysing the non-iodide carbonylation of methanol to acetic acid. However, the catalysts of Examples 1 and 2 where both aluminium and gallium are present in the mordenite structure much higher activities and selectivities to acetic acid and methyl acetate products can be achieved. The benefit of utilising both aluminium and gallium in the mordenite framework on product selectivity is further demonstrated in Table 2.

TABLE 2

Comparison of Product Selectivities for Cu/H—(Al) Mordenites and Cu/H—(Ga, Al) Mordenite Catalysts

| Catalyst | Catalyst SiO$_2$/Ga$_2$O$_3$ | Catalyst SiO$_2$/Al$_2$O$_3$ | Product Selectivity (C-mol %) | | | |
|---|---|---|---|---|---|---|
| | | | DME | HC | MeOAc | AcOH |
| Example 2 | 39.2 | 19.4 | 4.2 | 3.1 | 49.2 | 42.9 |
| Comparative Example B | — | 36.0 | 60.4 | 1.1 | 28.9 | 6.0 |
| Comparative Example C | — | 20.0 | 6.7 | 34.7 | 17.5 | 39.3 |

Reaction time = 6 hours. Reaction Temperature = 350° C., Pressure = 25 barg, GHSV = 4400, CO/MeOH = 9, LHSV = 0.9

It can be seen from Table 2 that high activity, as evidenced by low DME selectivity, and high selectivity to acetic acid and methyl acetate products can be achieved with the Ga and Al containing mordenite catalyst (Example 2) when compared to an aluminium only system which gives relatively high selectivities to hydrocarbon by-product at high framework aluminium content and low activity (as evidenced by the high amount of DME produced) at low framework aluminium content.

Table 3 demonstrates that considerable acetic acid and methyl acetate selectivity is retained for the catalysts of the present invention even after 70 hours on stream.

TABLE 3

Lifetime study for Example 1

| Time (hrs) | MeOH conversion (%) | Product Selectivity (C-mol %) | | | |
|---|---|---|---|---|---|
| | | DME | HC | MeOAc | AcOH |
| 3 | 99.5 | 0.0 | 22.8 | 6.9 | 68.2 |
| 6 | 98.2 | 1.2 | 7.5 | 34.8 | 52.6 |
| 26 | 93.1 | 41.2 | 1.2 | 39.9 | 17.5 |
| 59 | 86.4 | 61.1 | 0.3 | 30.4 | 8.1 |
| 68 | 88.7 | 77.4 | 0.7 | 15.2 | 6.6 |

Reaction Temperature = 350° C., Pressure = 25 barg, GHSV = 4400, CO/MeOH = 9, LHSV = 0.9

The invention claimed is:

1. A process for preparing an aliphatic carboxylic acid having (n+1) carbon atoms, where n is an integer up to 6, and/or an ester or anhydride thereof which process comprises contacting an aliphatic alcohol having n carbon atoms and/or a reactive derivative thereof with carbon monoxide substantially in the absence of the halogens or derivatives thereof and in the presence of a catalyst at a temperature in the range 250-600° C. and at a pressure in the range 10 to 200 bars, wherein the catalyst consists essentially of a mordenite which has, as framework elements, silicon, aluminium and one or more of gallium, boron and iron, and which has been ion-exchanged or otherwise loaded with copper, nickel, iridium, rhodium or cobalt.

2. A process according to claim 1 wherein the framework elements are silicon, aluminium and gallium.

3. A process according to claim 1 or claim 2 wherein the mordenite is ion-exchanged or loaded with copper.

4. A process according to claim 1 or claim 2 wherein the mordenite has a silica to alumina ratio in the range 10:1 to 30:1.

5. A process according to claim 1 or claim 2 wherein the mordenite has a ratio of silica to the oxides of gallium, boron and iron is in the range 20:1 to 50:1.

6. A process according to claim 5 wherein the ratio of silica to gallium oxide is in the range 20:1 to 50:1.

7. A process according to claim 1 or claim 2 wherein the mordenite is ion-exchanged with copper, nickel, iridium, rhodium or cobalt.

8. A process according to claim 7 wherein the mordenite has up to 80% of its exchangeable sites ion-exchanged with copper, nickel, iridium, rhodium or cobalt.

9. A process according to claim 1 or claim 2 wherein the catalyst has a metal content of 0.5 to 10% by weight based on the total weight of the catalyst.

10. A process according to claim 1 or claim 2 wherein the catalyst is activated prior to use.

11. A process according to claim 10 wherein the catalyst is activated by contacting the catalyst with flowing nitrogen, carbon monoxide or hydrogen for at least one hour at elevated temperature.

12. A process according to claim 1 or claim 2 wherein carbon monoxide and methanol vapour are fed through a fixed or fluidized bed of the catalyst substantially in the absence of iodide.

13. A process according to claim 1 or claim 2 wherein the aliphatic alcohol is methanol.

14. A process according to claim 13 wherein the methanol is generated from a mixture of carbon monoxide and hydrogen.

15. A process according to claim 14 wherein the methanol is generated in-situ.

16. A process according to claim 1 or claim 2 wherein dimethyl ether is employed as the reactive derivative.

17. A process according to claim 16 wherein a mixture of methanol and dimethyl ether is employed.

18. A process according to claim 16 and in which water is used as a feed to the process.

19. A process according to claim 18 wherein the water:dimethyl ether mole ratio is in the range (greater than 0) to less than or equal to 1.

20. A process according to claim 1 or claim 2 wherein the process is carried out in the substantial absence of water.

21. A process according to claim 1 or claim 2 wherein the process is carried out at a temperature in the range 250 to 400° C. and at a pressure in the range 10 to 150 bar.

22. A process according to claim 1 or claim 2 wherein the molar ratio of carbon monoxide to methanol is in the range 1:1 to 30:1.

23. A process according to claim 1 or claim 2 wherein the Liquid hourly space velocity of methanol is in the range 0.5 to 2.

24. A process for preparing acetic acid and/or ester or anhydride thereof which process comprises contacting methanol and/or a reactive derivative thereof with carbon monoxide substantially in the absence of halogens or derivates thereof and in the presence of a catalyst at a temperature in the range 250-600° C. and at a pressure in the range 10 to 200 bars, wherein the catalyst consists essentially of a mordenite which has, as framework elements, silicon, aluminium and gallium, and which has been ion-exchanged or otherwise loaded with copper, nickel, iridium, rhodium or cobalt.

25. A process according to claim 24 wherein the catalyst has been ion-exchanged or otherwise loaded with copper.

* * * * *

UNITED STATES PATENT AND TRADEMARK OFFICE
CERTIFICATE OF CORRECTION

| | | |
|---|---|---|
| PATENT NO. | : 7,642,372 B2 | Page 1 of 1 |
| APPLICATION NO. | : 11/578718 | |
| DATED | : January 5, 2010 | |
| INVENTOR(S) | : Warren John Smith | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this

Twenty-first Day of December, 2010

David J. Kappos
*Director of the United States Patent and Trademark Office*